United States Patent
Ellis et al.

(10) Patent No.: US 7,936,174 B2
(45) Date of Patent: *May 3, 2011

(54) COUPLING LOOP

(75) Inventors: Michael Ellis, Alpharetta, GA (US);
Jason Kroh, Villa Rica, GA (US);
Donald Miller, Roswell, GA (US)

(73) Assignee: CardioMEMS, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/545,166

(22) Filed: Aug. 21, 2009

(65) Prior Publication Data

US 2010/0026318 A1 Feb. 4, 2010

Related U.S. Application Data

(63) Continuation of application No. 11/668,601, filed on Jan. 30, 2007, now Pat. No. 7,595,647, which is a continuation of application No. 11/479,527, filed on Jun. 30, 2006, now Pat. No. 7,432,723, which is a continuation-in-part of application No. 11/105,294, filed on Apr. 13, 2005, now Pat. No. 7,245,117.

(60) Provisional application No. 60/623,959, filed on Nov. 1, 2004, provisional application No. 60/697,867, filed on Jul. 8, 2005, provisional application No. 60/697,878, filed on Jul. 8, 2005, provisional application No. 60/707,094, filed on Aug. 10, 2005.

(51) Int. Cl.
*G01R 27/28* (2006.01)

(52) U.S. Cl. ...................................... 324/654; 324/655

(58) Field of Classification Search .................. 324/654
See application file for complete search history.

(56) References Cited

U.S. PATENT DOCUMENTS

| | | | |
|---|---|---|---|
| 2,512,641 | A | 6/1950 | Halstead |
| 3,550,137 | A | 12/1970 | Kuecken |
| 3,651,243 | A | 3/1972 | Hornor et al. |
| 4,127,110 | A | 11/1978 | Bullara |
| 4,281,212 | A | 7/1981 | Bogese |
| 4,424,403 | A | 1/1984 | Bogese |
| 4,467,138 | A | 8/1984 | Brorein |
| 4,679,560 | A | 7/1987 | Galbraith |
| 5,043,531 | A | 8/1991 | Gutenson et al. |

(Continued)

FOREIGN PATENT DOCUMENTS

WO WO2007008493 1/2007

(Continued)

OTHER PUBLICATIONS

Chirlian, Basic Network Theory, McGraw Hill Book Co., 1969, Impedance section: p. 275-283, 350-355.*

*Primary Examiner* — Thomas Valone
(74) *Attorney, Agent, or Firm* — Kilpatrick Townsend & Stockton LLP

(57) ABSTRACT

A coupling loop or antenna is provided that can be used with a system that determines the resonant frequency of a sensor by adjusting the phase and frequency of an energizing signal until the frequency of the energizing signal matches the resonant frequency of the sensor. In one embodiment multiple energizing loops energize an implanted sensor and a sensor coupling loop connected to an input impedance that is at least two times greater than the inductance of the sensor coupling loop receives the sensor signal.

15 Claims, 14 Drawing Sheets

U.S. PATENT DOCUMENTS

| | | | |
|---|---|---|---|
| 5,153,583 | A | 10/1992 | Murdoch |
| 5,313,953 | A | 5/1994 | Yomtov |
| 5,491,299 | A | 2/1996 | Naylor et al. |
| 5,574,470 | A | 11/1996 | de Vall |
| 5,701,121 | A | 12/1997 | Murdoch |
| 5,976,070 | A | 11/1999 | Ono et al. |
| 6,009,350 | A | 12/1999 | Renken |
| 6,025,725 | A | 2/2000 | Gershenfeld et al. |
| 6,111,520 | A | 8/2000 | Allen et al. |
| 6,208,305 | B1 | 3/2001 | King |
| 6,252,163 | B1 | 6/2001 | Fujimori et al. |
| 6,278,379 | B1 | 8/2001 | Allen et al. |
| 6,298,271 | B1 | 10/2001 | Weijand |
| 6,448,500 | B1 | 9/2002 | Hosaka et al. |
| 6,777,940 | B2 | 8/2004 | Macune |
| 6,822,570 | B2 | 11/2004 | Dimmer et al. |
| 6,837,438 | B1 | 1/2005 | Takasugi et al. |
| 6,855,115 | B2 | 2/2005 | Fonseca et al. |
| 6,870,105 | B2 | 3/2005 | Maydanich et al. |
| 6,895,281 | B1 | 5/2005 | Amundson et al. |
| 6,898,454 | B2 | 5/2005 | Atalar et al. |
| 6,943,688 | B2 | 9/2005 | Chung et al. |
| 7,049,523 | B2 | 5/2006 | Shuman et al. |
| 7,208,684 | B2 | 4/2007 | Fetterolf, Sr. et al. |
| 7,215,991 | B2 | 5/2007 | Besson et al. |
| 7,245,117 | B1 | 7/2007 | Joy et al. |
| 7,432,723 | B2 * | 10/2008 | Ellis et al. ............... 324/654 |
| 7,439,723 | B2 * | 10/2008 | Allen et al. ............... 324/76.53 |
| 7,466,120 | B2 * | 12/2008 | Miller et al. ............... 324/76.51 |
| 7,498,799 | B2 * | 3/2009 | Allen et al. ............... 324/76.51 |
| 7,550,978 | B2 * | 6/2009 | Joy et al. ............... 324/633 |
| 7,595,647 | B2 * | 9/2009 | Kroh et al. ............... 324/654 |
| 7,679,355 | B2 * | 3/2010 | Allen et al. ............... 324/76.51 |
| 2003/0028094 | A1 | 2/2003 | Kumar et al. |
| 2003/0085799 | A1 | 5/2003 | Ghabra et al. |
| 2004/0036626 | A1 | 2/2004 | Chan et al. |
| 2004/0122494 | A1 | 6/2004 | Eggers et al. |
| 2004/0236209 | A1 | 11/2004 | Misic et al. |
| 2005/0075697 | A1 | 4/2005 | Olson et al. |
| 2006/0047327 | A1 | 3/2006 | Colvin et al. |
| 2006/0178586 | A1 | 8/2006 | Dobak |
| 2006/0244465 | A1 | 11/2006 | Kroh et al. |
| 2007/0118038 | A1 | 5/2007 | Bodecker et al. |
| 2007/0181331 | A1 | 8/2007 | Kroh et al. |
| 2007/0185546 | A1 | 8/2007 | Tseng et al. |
| 2007/0210786 | A1 * | 9/2007 | Allen et al. ............... 324/76.53 |
| 2007/0222603 | A1 | 9/2007 | Lai et al. |
| 2008/0029590 | A1 | 2/2008 | Zosimadis et al. |
| 2008/0061955 | A1 | 3/2008 | Tang et al. |
| 2008/0078567 | A1 | 4/2008 | Miller et al. |
| 2008/0081962 | A1 | 4/2008 | Miller et al. |
| 2009/0033486 | A1 | 2/2009 | Costantino |
| 2009/0224773 | A1 * | 9/2009 | Joy et al. ............... 324/633 |
| 2009/0278553 | A1 * | 11/2009 | Kroh et al. ............... 324/633 |

FOREIGN PATENT DOCUMENTS

| | | |
|---|---|---|
| WO | WO-2007008493 | 1/2007 |
| WO | WO2008031011 | 3/2008 |
| WO | WO-2008031011 | 3/2008 |
| WO | WO2008031095 | 3/2008 |
| WO | WO-2008031095 | 3/2008 |

* cited by examiner

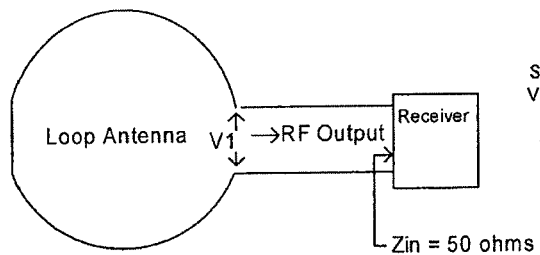
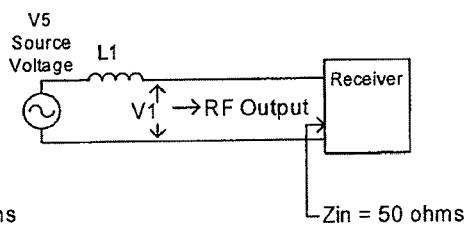
FIG. 5A  FIG. 5B
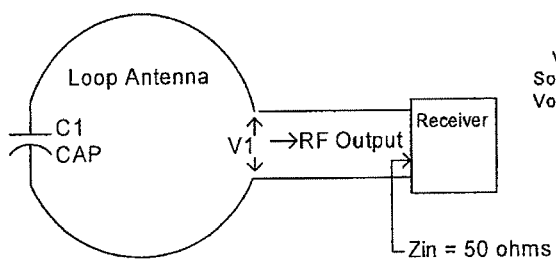
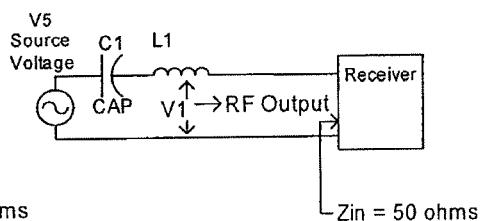
FIG. 6A  FIG. 6B
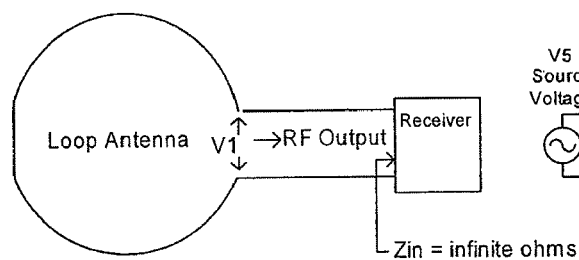
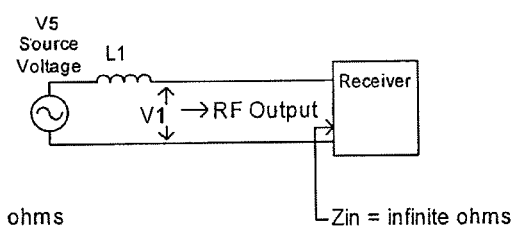
FIG. 7A  FIG. 7B ➕ Original Orientation ━ Rotated 90 along x axis ✚ Rotated 45 degrees along y axis

COUPLING LOOP

RELATED APPLICATIONS

This application is a continuation of U.S. application Ser. No. 11/668,601 entitled "Cable Assembly for a Coupling Loop", filed Jan. 30, 2007 which is a continuation of U.S. application Ser. No. 11/479,527, filed Jun. 30, 2006, now U.S. Pat. No. 7,432,723, which is a continuation-in-part of U.S. application Ser. No. 11/105,294, filed Apr. 13, 2005, now U.S. Pat. No. 7,245,117, entitled "Communicating with an Implanted Wireless Sensor", which claims priority to U.S. Provisional Application No. 60/623,959 entitled "Communicating with an Implanted Wireless Sensor" filed Nov. 1, 2004. U.S. application Ser. No. 11/479,527 claims priority to U.S. Provisional Application No. 60/697,867 entitled "Cable with Isolated Components" filed Jul. 8, 2005; U.S. Provisional Application No. 60/697,878 entitled "Antenna Sensor Location" filed Jul. 8, 2005 and U.S. Provisional Application No. 60/707,094 entitled "Broadband Transmit and Receive Antennas" filed Aug. 10, 2005. This application is related to U.S. application Ser. No. 11/276,571 entitled "Communicating with an Implanted Wireless Sensor" filed Mar. 6, 2006. All of the foregoing applications are incorporated herein by reference.

TECHNICAL FIELD

The present invention is directed in general to communicating with a wireless sensor, and in particular to a coupling loop and a cable used to communicate with a wireless sensor implanted within the body to measure a physical condition.

BACKGROUND

Wireless sensors can be implanted within the body and used to monitor physical conditions, such as pressure or temperature. For example, U.S. Pat. No. 6,111,520, U.S. Pat. No. 6,855,115 and U.S. Publication No. 2003/0136417, each of which is incorporated herein by reference, all describe wireless sensors that can be implanted within the body. These sensors can be used to monitor physical conditions within the heart or an abdominal aneurysm. An abdominal aortic aneurysm (AAA) is a dilatation and weakening of the abdominal aorta that can lead to aortic rupture and sudden death. In the case of a repaired abdominal aneurysm, a sensor can be used to monitor pressure within the aneurysm sac to determine whether the intervention is leaking. The standard treatment for AAAs employs the use of stent-grafts that are implanted via endovascular techniques. However, a significant problem that has emerged with these stent-grafts for AAAs is acute and late leaks of blood into the aneurysm's sac. Currently, following stent-graft implantation, patients are subjected to periodic evaluation via abdominal CT (Computed Tomography) with IV contrast to identify the potential presence of stent-graft leaks. This is an expensive, risky procedure that lacks appropriate sensitivity to detect small leaks.

Typically, the sensors utilize an inductive-capacitive ("LC") resonant circuit with a variable capacitor. The capacitance of the circuit varies with the pressure of the environment in which the sensor is located and thus, the resonant frequency of the circuit varies as the pressure varies. Thus, the resonant frequency of the circuit can be used to calculate pressure.

Ideally, the resonant frequency is determined using a non-invasive procedure. A system and method for determining the resonant frequency of an implanted sensor are discussed in U.S. application Ser. No. 11/276,571 entitled "Communicating with an Implanted Wireless Sensor" filed Mar. 6, 2006 (the '571 application"). The signal from the sensor is weak relative to the signal used to energize the sensor, but is the same frequency and dissipates quickly. In one embodiment, the difference between the signals is on the order of 150 dB and the sensor signal is sampled approximately 35 nanoseconds after the energizing signal is turned off. In order to communicate with the sensor, the system uses a coupling loop and a cable assembly. Due to the unique characteristics of the transmitted and received signals the coupling loop and the cable assembly need to isolate the energizing signal and the sensor signal, support the necessary sampling speed, and support a relatively large bandwidth.

Some prior art coupling loops use switched capacitor banks to meet the bandwidth requirement, but there are disadvantages to using switched capacitor banks regardless of the type of switching mechanism used. There are reliability issues associated with mechanical relays and loss issues associated with solid-state switches. Thus, there is a need for a coupling loop that provides the required bandwidth, but does not use switched capacitor banks.

A reflection or resonance from another object in the vicinity of the sensor can cause the system to lock on a frequency that does not correspond to the resonant frequency of the sensor, i.e. generates a false lock. Optimizing the position of the coupling loop relative to the sensor maximizes the coupling between the sensor and the coupling loop and reduces the sensitivity to a false lock. The coupling is maximized when the sensor is centered within the coupling loop and the inductor coil within the sensor is approximately parallel to the coupling loop. For many sensors this is achieved when the flat side of the sensor is approximately parallel to a plane defined by the coupling loop.

Thus, there is a need for indicating to a physician or other user the relative positions of the coupling loop and the sensor so that the sensor and the coupling loop are placed in magnetic proximity. In order to properly position the coupling loop, the coupling loop and the cable assembly should be easy to manipulate, which requires a lightweight coupling loop of a reasonable size and a flexible, lightweight cable with a relatively small diameter.

SUMMARY OF THE INVENTION

The primary goal of aneurysm treatment is to depressurize the sac and to prevent rupture. Endoleaks, whether occurring intraoperatively or postoperatively, can allow the aneurysmal sac to remain pressurized and therefore, increase the chance of aneurysm rupture. The current imaging modalities angiography and CT scan are not always sensitive enough to detect endoleaks or stent graft failure. Intrasac pressure measurements provide a direct assessment of sac exclusion from circulation and may therefore offer intraoperative and post operative surveillance advantages that indirect imaging studies do not.

In one application of the present invention, an AAA pressure sensor is placed into the aneurysm sac at the time of stent-graft insertion. The pressure readings are read out by the physician by holding an electronic instrument, which allows an immediate assessment of the success of the stent-graft at time of the procedure and outpatient follow-up visits, by reading the resonant frequency of the wireless sensor and correlating the frequency reading to pressure.

The present invention provides a coupling loop, a cable assembly and a method for positioning the coupling loop relative to the sensor that maximize the coupling between the sensor and the loop and that provide the necessary isolation between the energizing signal and the sensor signal. The system energizes the sensor with a low duty cycle, gated burst of RF energy having a predetermined frequency or set of frequencies and a predetermined amplitude. The energizing signal is coupled to the sensor via one or more energizing loops. Each energizing loop is tuned to a different resonant frequency. The selection of the resonant frequencies is based on the desired bandwidth, which in one aspect of the invention is 30-37.5 MHz. The sensor may be an inductive-capacitive ("LC") resonant circuit with a variable capacitor that is implanted within the body and used to measure physical parameters, such as pressure or temperature. The energizing signal induces a current in the sensor which is maximized when the energizing frequency is the same as the resonant frequency of the sensor. The system receives the ring down response of the sensor via one or more sensor coupling loops and determines the resonant frequency of the sensor, which is used to calculate the measured physical parameter. In one aspect of the invention, a single un-tuned sensor coupling loop is used. The loop is connected to an input impedance that is high relative to the loop inductance. In another aspect of the invention, multiple sensor coupling loops are used and each loop is tuned to a different resonant frequency.

The loops are connected to a base unit that generates the energizing signal and processes the sensor signal via a cable assembly. The cable assembly provides maximum isolation between the energizing signal and the sensor signal by maximizing the distance between the coaxial cables that carry the signals and maintaining the relative positions of the coaxial cables throughout the cable assembly. In one aspect of the invention, the coaxial cables are positioned on opposite sides of an internal cable, approximately 180 degrees apart. Shielding is also used to isolate the energizing signal from the sensor signal. In one aspect of the invention, additional shielding is provided around each of the coaxial cables.

Orientation features are provided for positioning the coupling loop relative to the sensor to maximize the coupling between the sensor and the coupling loop. The orientation features facilitate the placement of the sensor during implantation and the coupling loop during follow-up examinations. A physician typically uses fluoroscopy to implant the sensor in the patient. The sensor needs to be implanted in the proper anatomical location, e.g. within the aneurysm sac, and needs to be oriented to facilitate maximum coupling between the sensor and the coupling loop. In one aspect of the invention, the sensor and the coupling loop include orientation features that are visible using fluoroscopy or another medical imaging technology. The orientation features on the sensor include radiopaque markings and the orientation features on the coupling loop include a pattern in the ribbing of the housing for the loop.

To receive a signal from the sensor, the physician positions the coupling loop so that the sensor is approximately at the center of the coupling loop and adjusts the angle of the coupling loop until the inductor within the sensor and the coupling loop are approximately parallel. An orientation feature on the housing aids in positioning the coupling loop so that the sensor is at approximately the center of the loop and orientation features on either or both the sensor and the housing aid in adjusting the angle of the coupling loop so that the inductor within the sensor and the coupling loop are approximately parallel. The orientation features are designed to be visible using a medical imaging technology, such as fluoroscopy, x-ray, etc.

These and other aspects, features and advantages of the present invention may be more clearly understood and appreciated from a review of the following detailed description of the disclosed embodiments and by reference to the appended drawings and claims.

BRIEF DESCRIPTION OF THE DRAWINGS

FIG. 5A illustrates an un-tuned coupling loop and FIG. 5B illustrates its equivalent circuit.

FIG. 6A illustrates a tuned coupling loop and FIG. 6B illustrates its equivalent circuit.

FIG. 7A illustrates an un-tuned coupling loop terminated into a high impedance input and FIG. 7B illustrates its equivalent circuit in accordance with an embodiment of the invention.

DETAILED DESCRIPTION

The present invention is directed towards a coupling loop and cable assembly that supports precise sampling of a low power, quickly dissipating signal (the sensor signal) and that isolates the energizing signal used to excite the sensor from the sensor signal. The present invention also provides orientation features for positioning the coupling loop relative to the sensor to maximize the coupling of the sensor signal. Briefly described, the coupling loop includes multiple loops. Preferably two stagger-tuned loops are used for transmitting the energizing signal to the sensor and an un-tuned loop is used for receiving the sensor signal from the sensor. The un-tuned loop is connected to a very high input impedance to minimize the impact of the inductance of the loop. A cable attached to the coupling loop provides maximum isolation between the energizing signal and the sensor signal by maximizing the distance between the coaxial cables that carry the signals and maintaining the relative positions of the coaxial cables throughout the cable assembly. A method for positioning the coupling loop relative to the sensor is provided that maximizes the coupling between the sensor signal and the coupling loop.

Exemplary Operating Environment

Figure 1:
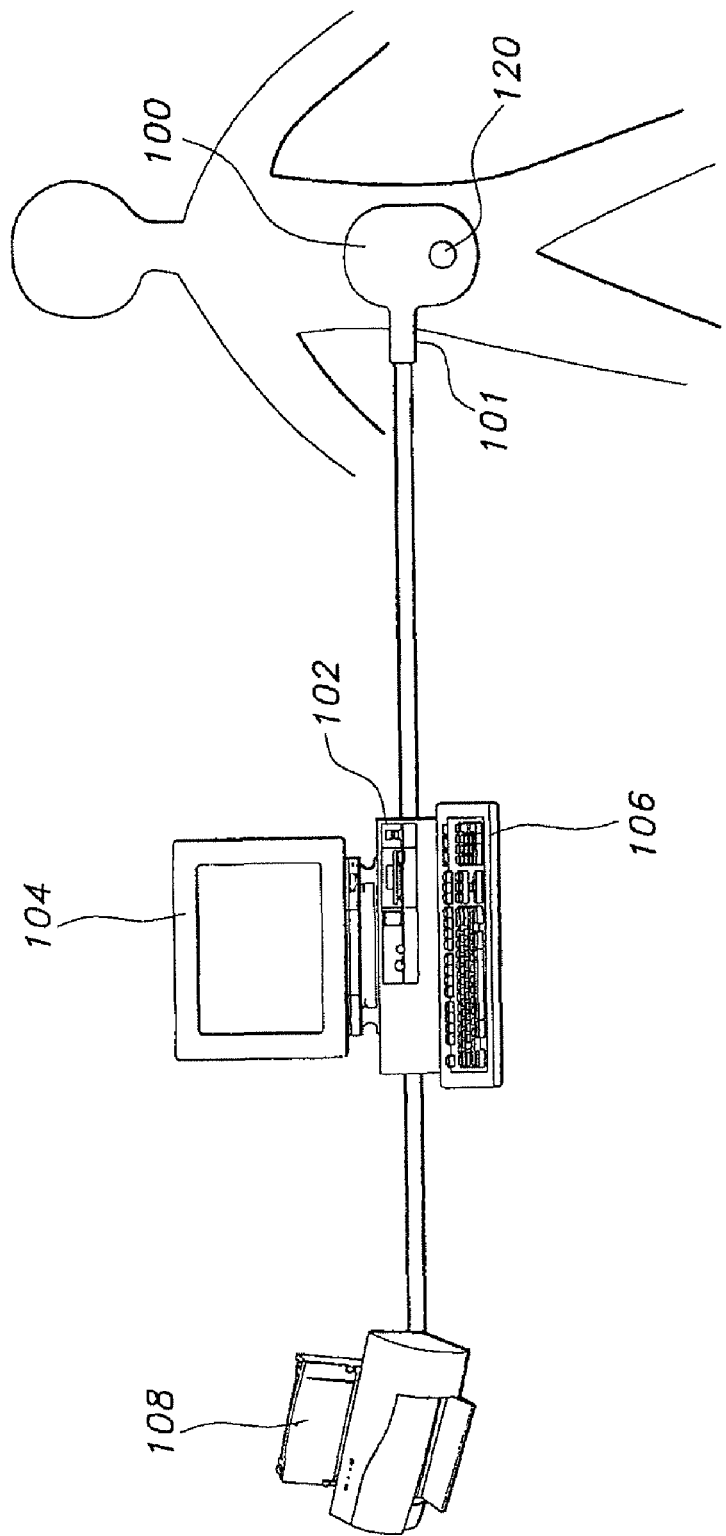
FIG. 1 is a block diagram of an exemplary system for communicating with a wireless sensor in accordance with an embodiment of the invention.

FIG. 1 illustrates an exemplary system for communicating with a wireless sensor implanted within a body. The system includes a coupling loop 100, a base unit 102, a display device 104 and an input device 106, such as a keyboard. The base unit includes an RF amplifier, a receiver, and signal processing circuitry. Additional details of the circuitry are described below in connection with FIG. 3.

The display 104 and the input device 106 are used in connection with the user interface for the system. In the embodiment illustrated in FIG. 1 the display device and the input device are connected to the base unit. In this embodiment, the base unit also provides conventional computing functions. In other embodiments, the base unit can be connected to a conventional computer, such as a laptop, via a communications link, such as an RS-232 link. If a separate computer is used, then the display device and the input devices associated with the computer can be used to provide the user interface. In one embodiment, LABVIEW software is used to provide the user interface, as well as to provide graphics, store and organize data and perform calculations for calibration and normalization. The user interface records and displays patient data and guides the user through surgical and follow-up procedures. An optional printer 108 is connected to the base unit and can be used to print out patient data or other types of information. As will be apparent to those skilled in the art other configurations of the system, as well as additional or fewer components can be utilized with the invention.

Figure 2:
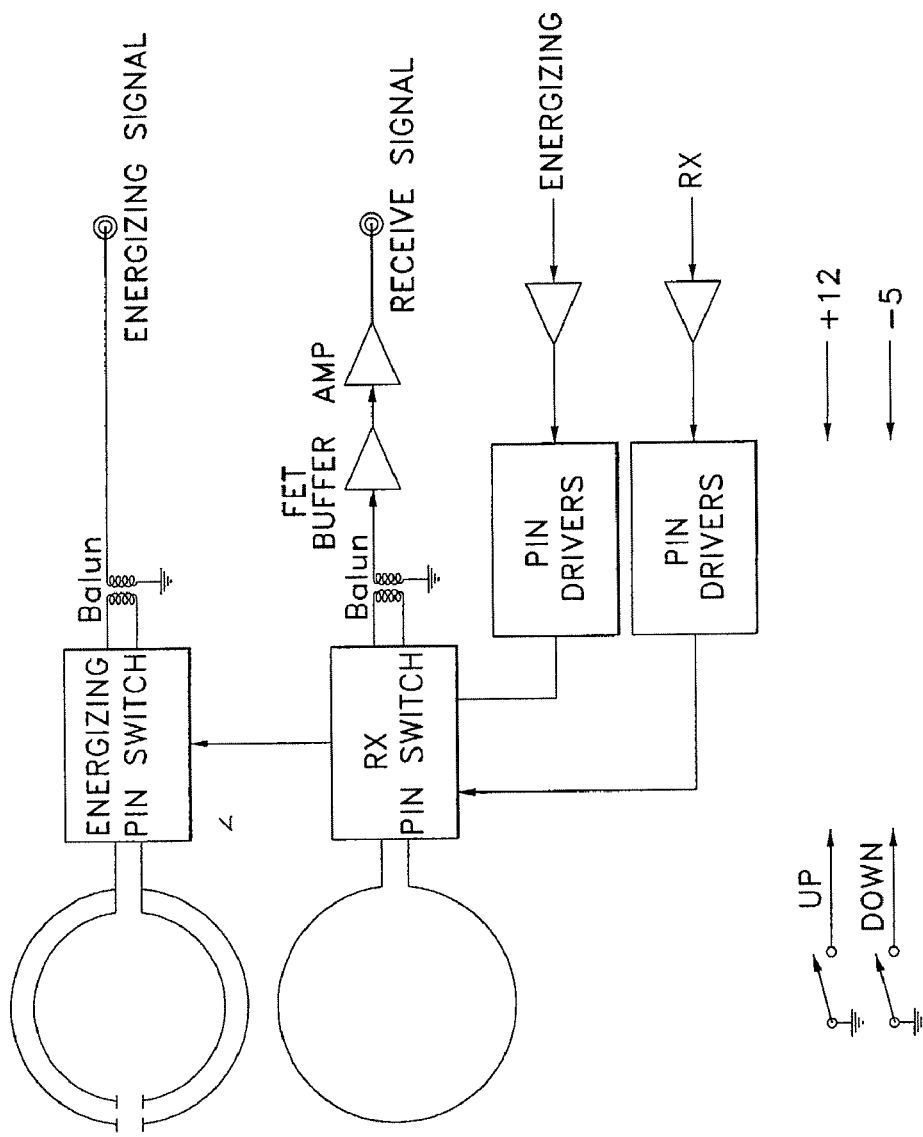
FIG. 2 is a block diagram of an exemplary coupling loop assembly for communicating with a wireless sensor in accordance with an embodiment of the invention.

The coupling loop 100 charges the sensor 120 and then couples signals from the sensor into the receiver. The coupling loop can include switching and filtering circuitry enclosed within a shielded box 101. In the embodiment illustrated by FIG. 2, PIN diode switching inside the loop assembly is used to provide isolation between the energizing phase and the receive phase by opening the RX path pin diodes during the period when the energizing signal is transmitted to the sensor, and opening the energizing path pin diodes during the period when the sensor signal is received from the sensor. Additional details of the coupling loop and the cable that connects the coupling loop to the base unit are described below.

FIG. 1 illustrates the system communicating with a sensor 120 implanted in a patient. Each sensor is associated with a number of calibration parameters, such as frequency, offset, and slope. The system is used in two environments: 1) the operating room during implant and 2) the physician's office during follow-up examinations. During implant the system is used to record at least two measurements. The first measurement is taken during introduction of the sensor for calibration and the second measurement is taken after placement for functional verification of the stent graft. The measurements can be taken by placing the coupling loop either on or adjacent to the patient's back or the patient's stomach for a sensor that measures properties associated with an abdominal aneurysm. For other types of measurements, the coupling loop may be placed in other locations. For example, to measure properties associated with the heart, the coupling loop can be placed on the patient's back or the patient's chest.

The system communicates with the implanted sensor to determine the resonant frequency of the sensor. As described in more detail in the patent documents referenced in the Background section, a sensor typically includes an inductive-capacitive ("LC") resonant circuit having a variable capacitor. The distance between the plates of the variable capacitor varies as the surrounding pressure varies. Thus, the resonant frequency of the circuit can be used to determine the pressure.

Figures 3A, 3B, 3C, 3D:
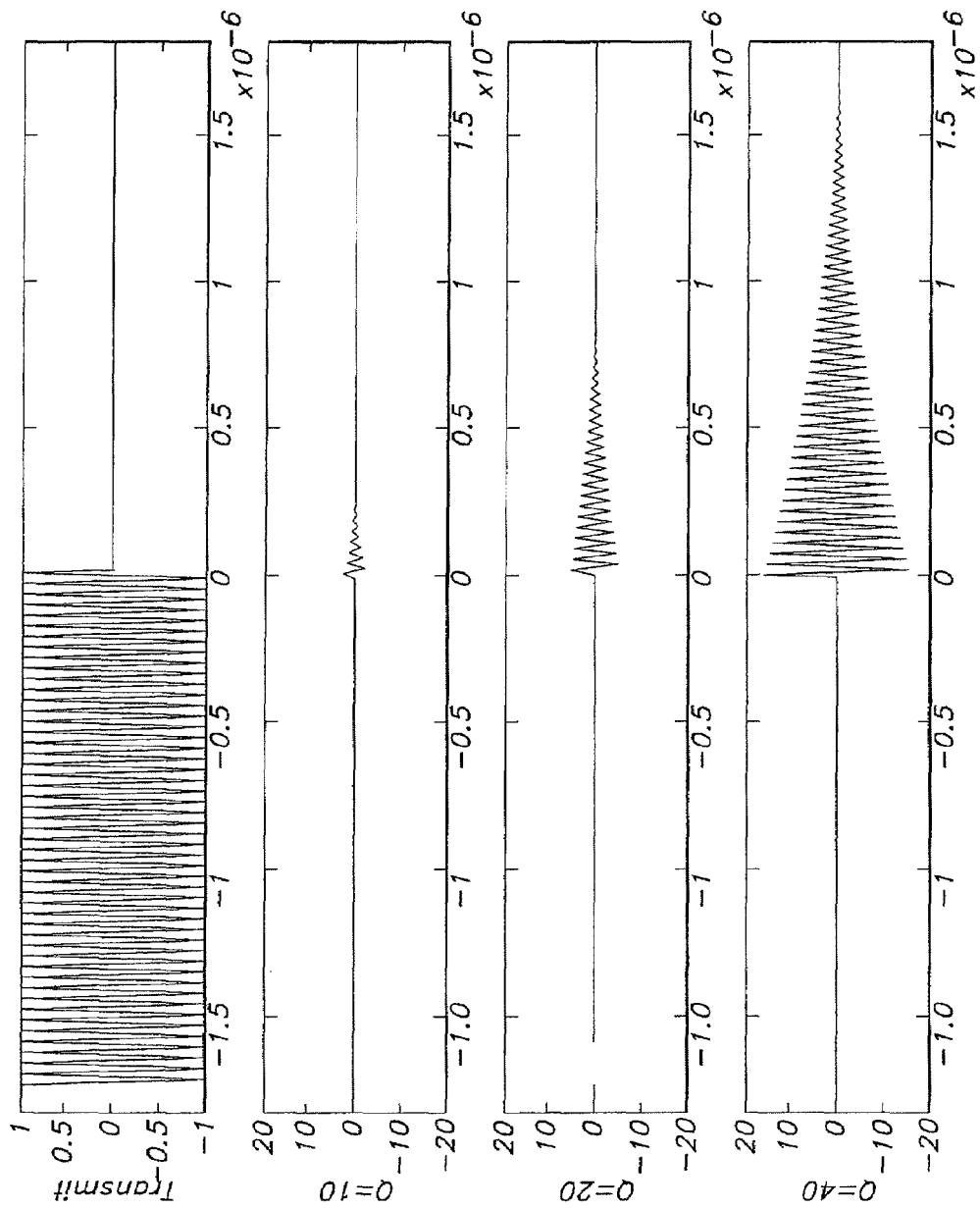
FIG. 3(a) is a graph illustrating an exemplary energizing signal in accordance with an embodiment of the invention.
FIGS. 3(b), 3(c) and 3(d) are graphs illustrating exemplary coupled signals in accordance with an embodiment of the invention.

The system energizes the sensor with an RF burst. The energizing signal is a low duty cycle, gated burst of RF energy of a predetermined frequency or set of frequencies and a predetermined amplitude. Typically, the duty cycle of the energizing signal ranges from 0.1% to 50%. In one embodiment, the system energizes the sensor with a 30-37.5 MHz fundamental signal at a pulse repetition rate of 100 kHz with a duty cycle of 20%. The energizing signal is coupled to the sensor via the coupling loop. This signal induces a current in the sensor which has maximum amplitude at the resonant frequency of the sensor. During this time, the sensor charges exponentially to a steady-state amplitude that is proportional to the coupling efficiency, distance between the sensor and loop, and the RF power. FIG. 3($a$) illustrates a typical energizing signal and FIGS. 3($b$), 3($c$) and 3($d$) illustrate typical coupled signals for various values of Q (quality factor) for the sensor. When the coupling loop is coupling energy at or near the resonant frequency of the sensor, the amplitude of the sensor return is maximized, and the phase of the sensor return will be close to zero degrees with respect to the energizing phase. The sensor return signal is processed via phase-locked-loops to steer the frequency and phase of the next energizing pulse.

Operation of the Base Unit

Figure 4:
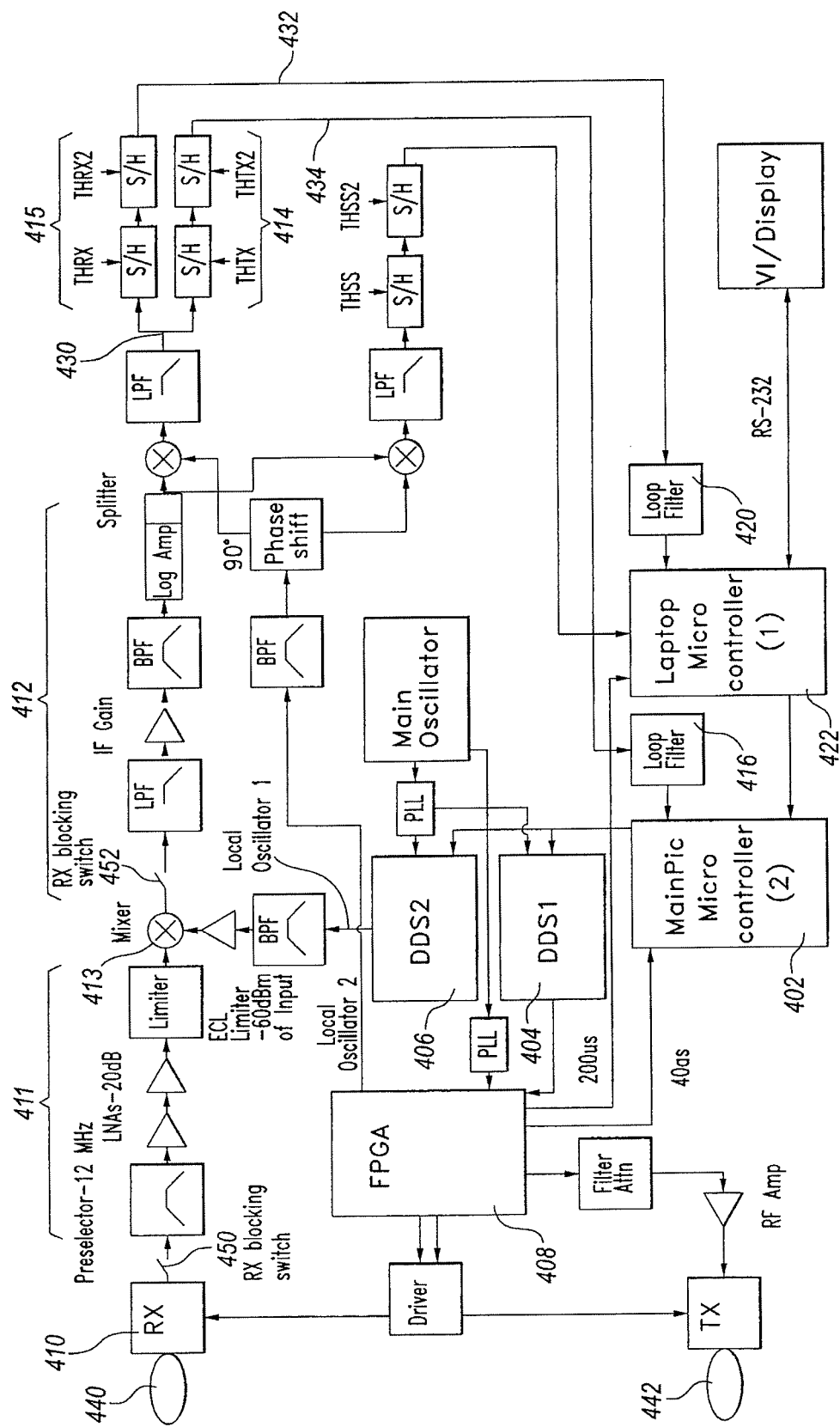
FIG. 4 is a block diagram of an exemplary base unit in accordance with an embodiment of the invention.

FIG. 4 is a block diagram of the signal processing components within an exemplary base unit. The base unit determines the resonant frequency of the sensor by adjusting the energizing signal so that the frequency of the energizing signal matches the resonant frequency of the sensor. In the embodiment illustrated by FIG. 4, two separate processors 402, 422 and two separate coupling loops 440, 442 are shown. In one embodiment, processor 402 is associated with the base unit and processor 422 is associated with a computer connected to the base unit. In other embodiments, a single processor is used that provides the same functions as the two separate processors. In other embodiments a single loop is used for both energizing and for coupling the sensor energy back to the receiver. As will be apparent to those skilled in the art, other configurations of the base unit are possible that use different components.

The embodiment illustrated by FIG. 4 includes a pair of phase lock loops ("PLL"). One of the PLLs is used to adjust the phase of the energizing signal and is referred to herein as the fast PLL. The other PLL is used to adjust the frequency of the energizing signal and is referred to herein as the slow PLL. The base unit provides two cycles: the calibration cycle and the measurement cycle. In one embodiment, the first cycle is a 10 microsecond energizing period for calibration of the system, which is referred to herein as the calibration cycle, and the second cycle is a 10 microsecond energizing/coupling period for energizing the sensor and coupling a return signal from the sensor, which is referred to herein as the measurement cycle. During the calibration cycle, the system generates a calibration signal for system and environmental phase calibration and during the measurement cycle the system both sends and listens for a return signal, i.e. the sensor ring down. Alternatively, as those skilled in the art will appreciate, the calibration cycle and the measurement cycle can be implemented in the same pulse repetition period. The phase of the energizing signal is adjusted during the calibration cycle by the fast PLL and the frequency of the energizing signal is adjusted during the measurement cycle by the slow PLL.

In one embodiment, the calibration signal is the portion of the energizing signal that leaks into the receiver (referred to herein as the energizing leakage signal). In this embodiment, the signal is sampled approximately 100 ns after the beginning of the energizing signal pulse. Since the energizing signal is several orders of magnitude greater than the coupled signal, it is assumed that the phase information associated with the leaked signal is due to the energizing signal and the phase delay is due to the circuit elements in the coupling loop, circuit elements in the receiver, and environmental conditions, such as proximity of reflecting objects. During the calibration cycle, the phase difference between the leaked signal and a reference oscillator (local oscillator 2) is determined. The phase of the energizing signal is adjusted until the phase difference is zero or another reference phase.

During the measurement cycle, the energizing signal may be blocked from the receiver during the on time of the energizing signal. During the off time of the energizing signal, the receiver is unblocked and the coupled signal from the sensor (referred to herein as the coupled signal or the sensor signal) is received. The coupled signal is processed and is used to drive the output of the slow PLL loop filter to a preset value.

The frequency of the energizing signal is deemed to match the resonant frequency of the sensor when the slow PLL is locked. Once the resonant frequency is determined, the physical parameter, such as pressure, is calculated using the calibration parameters associated with the sensor, which results in a difference frequency that is proportional to the measured pressure. Additional details of the operation of the PLLs are provided in the '571 application.

Coupling Loop Assembly

In the present invention, the coupling loop or antenna provides isolation between the energizing signal and the sensor signal, supports sampling/reception of the sensor signal very soon after the end of the energizing signal, and minimizes the switching transients that result from switching between the energizing and the coupled mode. The coupling loop also provides a relatively wide bandwidth, for example 30-37.5 MHz.

In one embodiment, separate loops are used for transmitting the energizing signal to the sensor and coupling the signal from the sensor. Two stagger-tuned loops are used to transmit the energizing signal and an un-tuned loop with a high input impedance at the receiver is used to receive the sensor signal. The term "coupling loop" is used herein to refer to both the loop(s) used to receive the sensor signal from the sensor (the "sensor coupling loop"), as well as the assembly that includes the loop(s) used to transmit the energizing signal to the sensor (the "energizing loop") and the sensor coupling loop(s).

During the measurement cycle, the sensor coupling loop couples the signal from the sensor, which is weak and dissipates quickly. The voltage provided to the receiver in the base unit depends upon the design of the sensor coupling loop and in particular, the resonant frequency of the loop.

A coupling loop can be un-tuned or tuned. FIG. 5A illustrates a loop that is un-tuned and FIG. 5B illustrates its equivalent circuit. The loop has an inductance, $L_1$, and is terminated into the receiver using a common input impedance of 50 ohms. The voltage at the receiver, $V_1$, is less than the open circuit voltage of the loop, i.e. the voltage that would be coupled by the loop if the loop was not terminated, $V_s$, and can be calculated as shown below.

$$V_1 = V_s \frac{50}{50 + j\omega L_1}$$

Where $L_1$ is the inductance of the loop and $\omega = 2\pi f$, with f=frequency in hertz.

To maximize the voltage at the receiver, the loop can be tuned. FIG. 6A illustrates a loop that is tuned and FIG. 6B illustrates its equivalent circuit. The loop has an inductance, $L_1$, and a capacitance, $C_1$. The capacitance, $C_1$, is selected so that it cancels the inductance, $L_1$ at the resonant frequency, i.e. the series resonant circuit, $C_1$-$L_1$, is 0 ohms at the resonant frequency. At the resonant frequency the voltage at the receiver, $V_1$, equals the voltage coupled by the loop, $V_s$. A disadvantage of this type of loop is that it is optimized for only a single frequency. If the loop is used in an environment where the frequency of the coupled signal is changing, then the capacitance is either changed dynamically or set to a compromise value (e.g. the loop is tuned to a single frequency within the band of interest).

To avoid these problems, the present invention uses an un-tuned loop with a high input impedance at the receiver. FIG. 7A illustrates a loop terminated into a receiver with a high input impedance and FIG. 7B illustrates its equivalent circuit. The input impedance at the receiver is selected so that the energy lost due to the loop impedance, $L_1$, is relatively insignificant. Using Zin as the input impedance at the receiver, the voltage at the receiver, $V_1$, is calculated as shown below.

$$V_1 = V_s \frac{Zin}{Zin + j\omega L_1}$$

Since Zin is much larger than $j\omega L_1$, this can be approximated by the following.

$$V_1 = V_s \frac{\infty}{\infty + j\omega L_1}, \text{ or } V_1 = V_s$$

As shown by the foregoing equation, the use of a relatively high input impedance at the input of the receiver negates $L_1$ for all frequencies. In one embodiment, a high impedance buffer is inserted between the loop and a 50 ohm receiver circuit. In this embodiment, the high impedance buffer is on the order of 1 Mohm while the impedance of the loop is on the order of 200 ohms. In other embodiments, the input impedance is at least two times the loop impedance.

Figure 8:
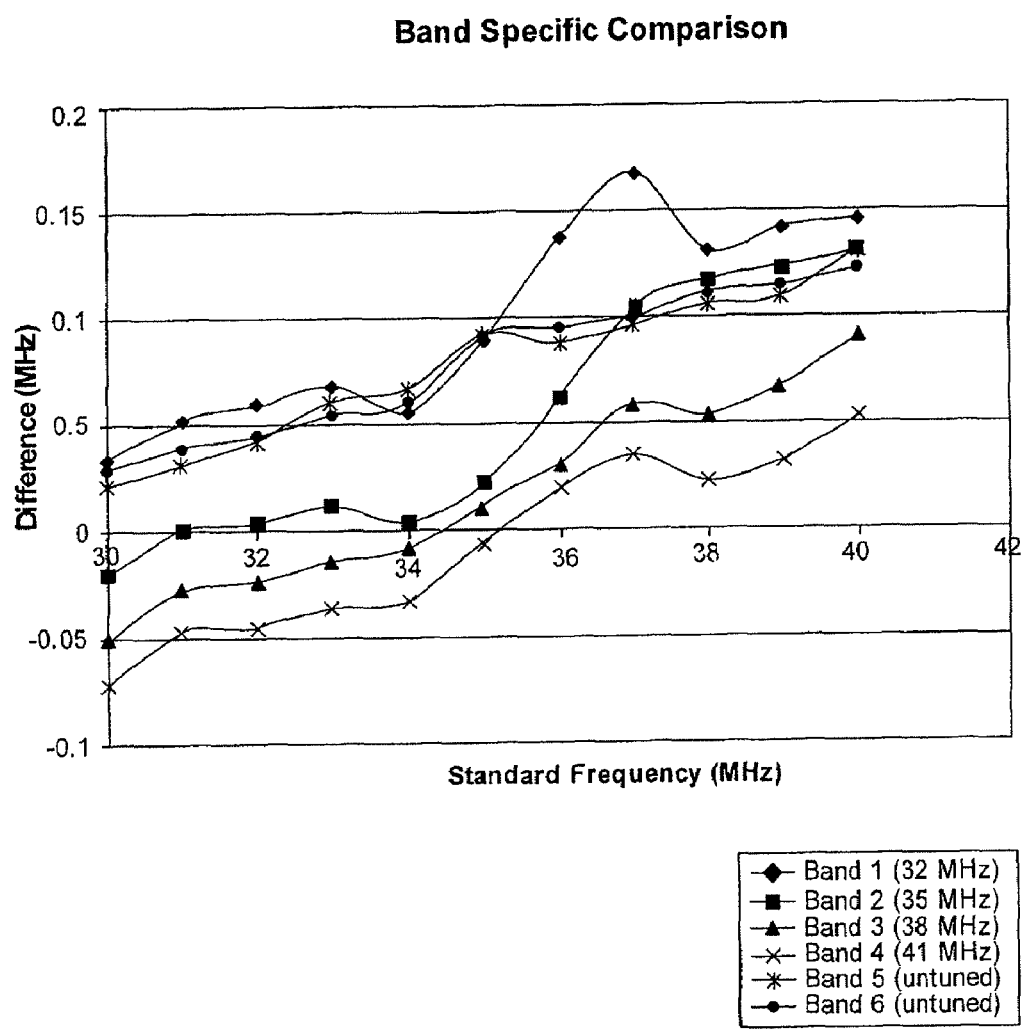
FIG. 8 is a graph illustrating the frequency response for various loops within the frequency band of interest.

The frequency response within the band of interest is more monotonic if the sensor coupling loop uses a high input impedance at the receiver, than if a tuned loop is used with a 50 ohm input impedance. FIG. 8 compares the frequency response for tuned loops and the frequency response for un-tuned loops with high input impedances at the receiver. The y-axis represents the difference in measured frequency between a calibration system using a network analyzer and the loop. The x-axis represents the frequency of the L-C standard used in the measurements. Linear interpolation was used between measurement points. Band 1 corresponds to a loop resonant at 32 MHz, Band 2 corresponds to a loop resonant at 35 MHz, Band 3 corresponds to a loop resonant at 38 MHz and Band 4 corresponds to a loop resonant at 41 MHz. Bands 1-4 correspond to a prior art design that uses switched capacitors banks to vary the loop resonance to achieve the needed bandwidth. Bands 4 and 5 correspond to un-tuned loops.

Bands 1-4 illustrate a slope variation within the band of interest, which can affect the accuracy of measurements made using the loop. Bands 4 and 5 illustrate that the variation within the band of interest is less than in the systems using a tuned loop. The more monotonic frequency response of an un-tuned loop with a high input impedance requires a simpler set of calibration coefficients to be used for the frequency conversion calculation.

An alternative to using an un-tuned loop and a high input impedance is to use stagger-tuned loops. If stagger tuned loops are used to receive the sensor signal, then the loops are tuned in a manner similar to that described in the following paragraphs in connection with the transmission of an energizing signal.

During the energizing mode, the energizing loop produces a magnetic field. The intensity of the magnetic field produced by the energizing loop depends, in part, on the magnitude of the current within the loop. The current is maximized at the energizing frequency if the impedance of the loop is essentially 0 ohms at the energizing frequency. The resonant frequency of the loop is related to the loop inductance and capacitance, as shown below.

$$f_o = \frac{1}{2\pi\sqrt{L*C1}}$$

Figure 9:
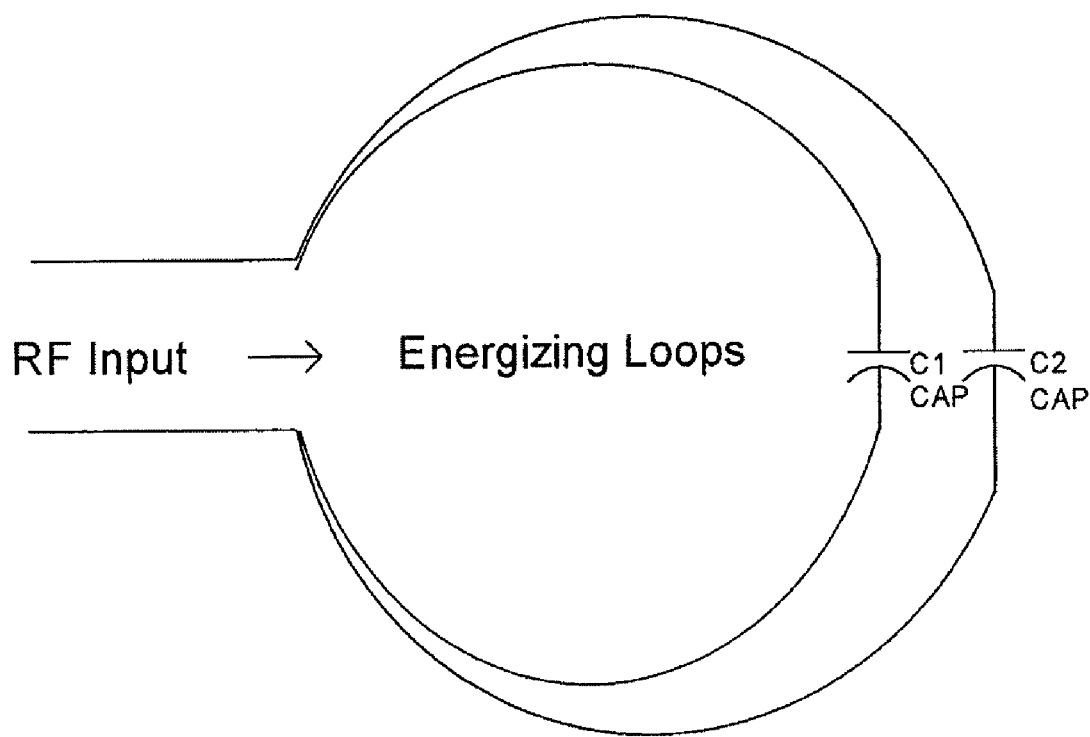
FIG. 9 illustrates exemplary energizing loops in accordance with an embodiment of the invention.

The impedance of the loop is preferably 0 ohms over the frequency range of interest, which in an exemplary operating environment of the present invention is 30 MHz to 37.5 MHz. To achieve the desired impedance over the desired frequency range, two or more loops are stagger tuned. FIG. 9 illustrates two stagger-tuned loops, which are parallel to one another.

The resonant frequencies for the loops are based on the bandwidth of interest. If there are two loops, then the loops are spaced geometrically. In one embodiment, the resonant frequency of the first loop is 31 MHz and the resonant frequency of the second loop is 36.3 MHz, which corresponds to the pole locations of a second order Butterworth bandpass filter having −3 dB points at 30 MHz and 37.5 MHz. Although FIG. 9 illustrates two loops, other embodiments can use a different number of loops. The use of additional loops provides coverage for a much wider frequency range. If there are more than two loops, then the loops are spaced logarithmically.

Figure 10:
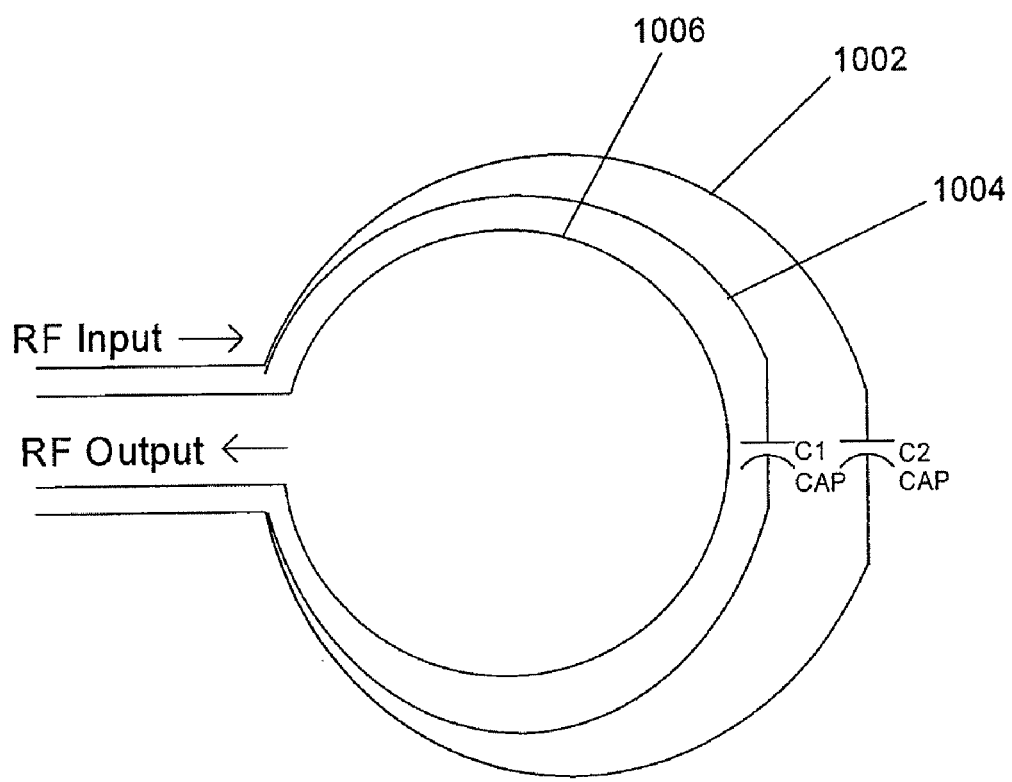
FIG. 10 illustrates exemplary energizing and sensor coupling loops in accordance with an embodiment of the invention.

FIG. 10 illustrates the assembly of two stagger-tuned loops 1002, 1004 for transmitting the energizing signal to the sensor and one un-tuned loop 1006 for receiving the sensor signal. The loops are parallel to one another with the un-tuned loop inside the stagger-tuned loops. Placing the loop used to receive the sensor signal inside of the loops used to transmit the energizing signal helps to shield the sensor signal from environmental interferences. In one embodiment, the loops are positioned within a housing, such as that shown in FIG. 11.

Positioning the Coupling Loop

The signal from an implanted passive sensor is relatively weak and is attenuated by the surrounding tissue and the distance between the sensor and the coupling loop. Optimizing the position and angle of the coupling loop relative to the sensor maximizes the coupling between the sensor and the coupling loop. In particular, the coupling loop is positioned so that a plane defined by the sensor coupling loop is approximately parallel to the inductor within the sensor and the sensor is approximately centered within the sensor coupling loop. For sensors having an inductor parallel to the flat side of the sensor, this corresponds to positioning the coupling loop so that it is approximately parallel to the flat side of the sensor. If the coupling loop is not positioned in this manner relative to the inductor, then the strength of the sensor signal is reduced by the cosine of the angle between the sensor coupling loop and the flat side of the sensor (assuming the inductor within the sensor is parallel to the flat side of the sensor).

The sensor and/or the housing include orientation features, which are visible using a medical imaging technology, such as fluoroscopy, to facilitate the placement of the sensor during implantation and the coupling loop during follow-up examinations. To position the coupling loop relative to the sensor, the coupling loop is moved or adjusted until a predetermined pattern appears. As previously described, measurements are typically taken by placing the coupling loop either on or adjacent to the patient's back or stomach for an abdominal aneurysm. To facilitate these measurements and to minimize the distance between the sensor and the coupling loop, the sensor should be implanted so that the inductor within the sensor is approximately horizontal when the patient is standing.

Figure 11:
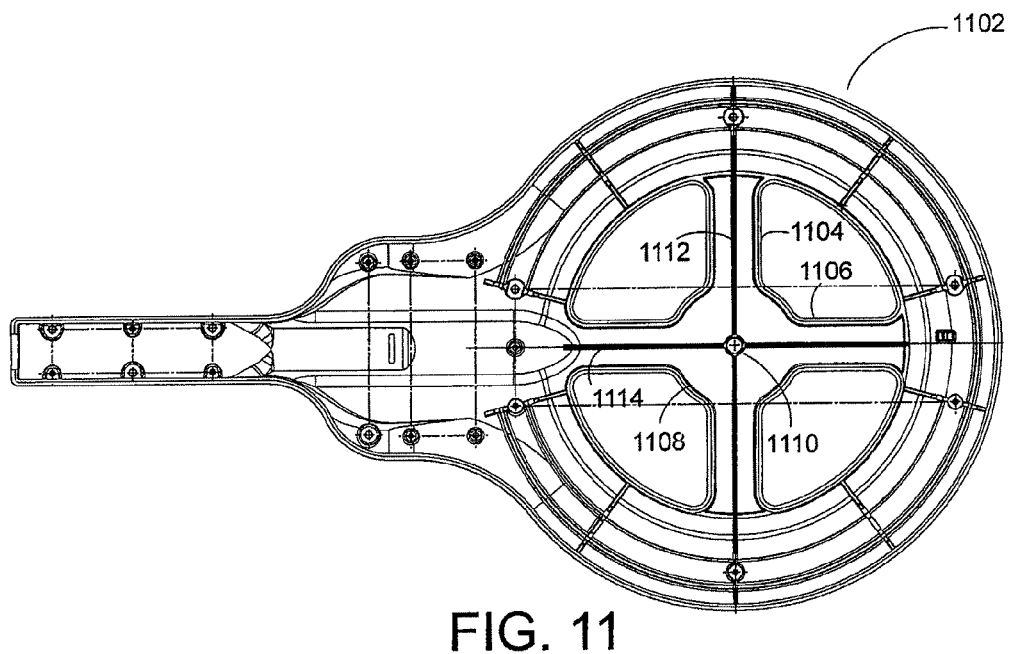
FIG. 11 illustrates an exemplary coupling loop housing in accordance with an embodiment of the invention.

The orientation features on the coupling loop can be implemented as a pattern in the ribbing of the housing for the loop. Ribbing is typically used to strengthen and support plastic enclosures or housings. In the present invention, the ribbing is formed so that it aids in positioning the coupling loop relative to the sensor. FIG. 11 is a cross sectional view of an exemplary housing that includes a ring-shaped section 1102 with perpendicular cross supports 1104, 1106 in the interior of the ring-shaped section. At the point where the cross supports intersect, the housing includes an essentially circular section 1108. The diameter of section 1108 is smaller than the diameter of section 1102. When assembled, the sensor coupling and energizing loops are positioned within the ring-shaped section. The orientation features are located in the circular section 1108. FIG. 11 illustrates a circular orientation feature 1110 at the center of the circular section 1108. The ribbing for the cross supports 1112, 1114 can also form part of the orientation feature.

Although FIG. 11 illustrates a particular design for the housing, other designs are possible, so long as the housing provides the necessary orientation features. For example, FIG. 11 illustrates that there are four open spaces essentially corresponding to four quadrants defined by the cross supports in the interior of the ring-shaped section. These spaces reduce the amount of material needed to form the enclosure and thus minimize the weight of the enclosure, but are not required by the present invention for positioning the loop.

The orientation features on the sensor can be implemented as radiopaque markings on the essentially flat sides of the sensor. The references herein to the flat side of the sensor assume that the inductor within the sensor is parallel to the flat side of the sensor. As those skilled in the art will understand, the purpose of the orientation features is to position the coupling loop approximately parallel to the inductor within the sensor. If the inductor is not parallel to the flat side of the sensor, then the desired position of the coupling loop relative to the side of the sensor may differ.

Figure 12:
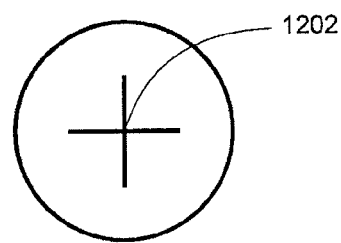
FIG. 12 illustrates an exemplary sensor in accordance with an embodiment of the invention.

Typically, the sensor is disk-shaped. The flat sides of the disk are essentially parallel and may be of any shape including circular, oval, rectangular, or daisy-shaped. FIG. 12 illustrates a sensor with circular sides. The sensor includes an orientation feature 1202 at the center of the sensor that is shaped like a cross where each cross bar is essentially equal in length.

To receive a signal from the sensor, the physician positions the coupling loop so that the sensor is approximately at the center of the coupling loop and adjusts the angle of the coupling loop until the flat side of the sensor and the coupling loop are approximately parallel, which places the inductor coil within the sensor essentially parallel to the coupling loop. The orientation feature on the housing aids in positioning the coupling loop so that the sensor is at approximately the center of the loop. If the housing illustrated in FIG. 11 is used, then the physician moves the coupling loop until the sensor appears within the circular orientation feature 110. The orientation feature on the sensor aids in adjusting the angle of the coupling loop so that the flat side of the sensor and the coupling loop are approximately parallel. If the sensor illustrated in FIG. 12 is used, then the angle of the coupling loop is adjusted until the cross appears.

Figure 13:
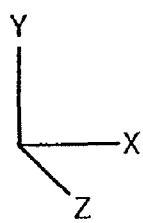
FIG. 13 illustrates an exemplary orientation feature in accordance with an embodiment of the invention.

The cross appears when the coupling loop is essentially parallel to the flat side of the sensor. As shown in FIG. 13, if the coupling loop is not essentially parallel to the flat side of the sensor, then the cross is distorted. If the cross is distorted, then the coupling loop is rotated until the cross appears. For example, if the vertical cross bars in FIG. 13 are shortened or not visible, then the physician rotates the coupling loop around the x-axis until the vertical cross bars appear with the proper length. Similarly, if the horizontal cross bars in FIG. 13 are shortened or not visible, then the physician rotates the coupling loop around the y-axis until the horizontal cross bars appear with the proper length.

Figure 14A:
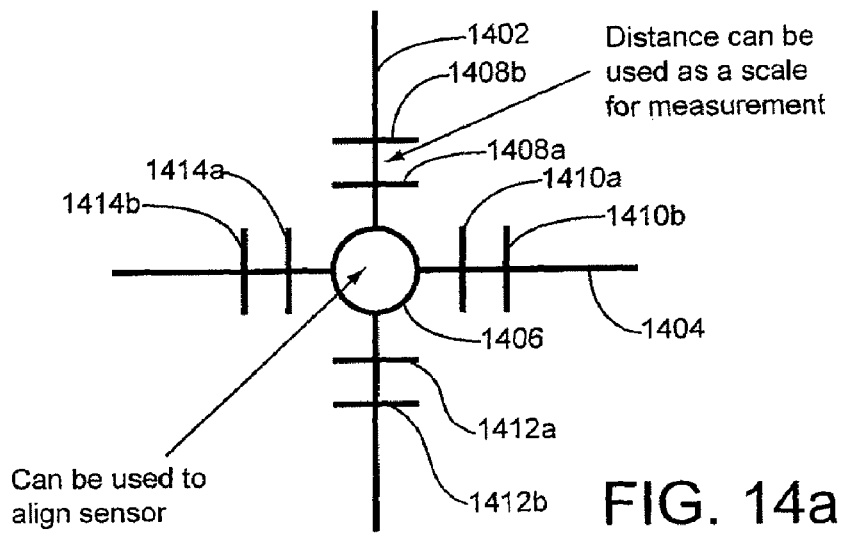
FIGS. 14a and 14b illustrate another exemplary orientation feature in accordance with an embodiment of the invention.
Figure 14B:
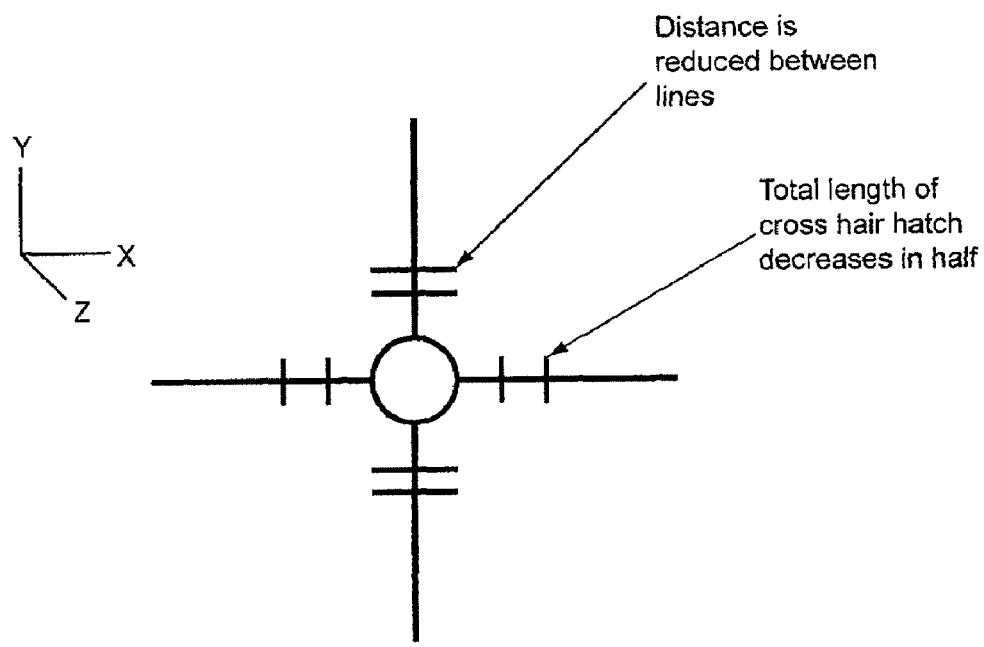

FIGS. 14a and 14b show the effects of misalignment for another orientation feature. This feature uses a cross hair design. The perpendicular lines 1402, 1404 and the circle 1406 are orientation marks on the housing and the cross hairs 1408a, 1408b, 1410a, 1410b, 1412a, 1412b, 1414a, and 1414b are orientation marks on the sensor. FIG. 14a illustrates the desired pattern. If the coupling loop is not essentially parallel to the flat side of the sensor, then the cross hairs are distorted. If the cross hairs are distorted, then the coupling loop is rotated until the cross hairs appear properly. For example, if the vertical cross bars 1410a, 1410b, 1414a, 1414b are shortened or not visible and the horizontal cross bars 1408a, 1408b, 1412a, 1412b are not properly spaced, then the physician rotates the coupling loop around the x-axis until the vertical cross bars appear with the proper length and the horizontal cross bars appear with the proper spacing. FIG. 14b illustrates the cross hairs when the coupling loop is rotated 45 degrees along the x-axis. Similarly, if the horizontal cross bars are shortened or not visible and the vertical cross bars are not properly spaced, then the physician rotates the coupling loop around the y-axis until the horizontal cross bars appear with the proper length and the vertical cross bars appear with the proper spacing.

In one embodiment, the housing includes an orientation feature that matches or complements the orientation feature on the sensor. If the housing includes a matching feature, then the coupling loop is properly positioned when the orientation feature on the housing aligns with, is equal to, or otherwise matches the orientation feature on the sensor. If the housing includes a complementary feature, such as the cross hair design illustrated by FIG. 14a, then the coupling loop is properly positioned when a predetermined pattern appears that is a combination of the orientation feature on the sensor and the orientation feature on the housing. As an alternative to matching or aligning the orientation features of the sensor and the housing, the physician can measure a part of or the entire orientation feature. For example, the physician could move the coupling loop until the distance between two bars equals a predetermined distance as measured using a fluoroscope.

Although the foregoing describes a circular orientation feature, a cross-shaped orientation feature, and a cross hair orientation feature, other patterns, shapes and types of orientation features can be used, including a bull's eye, logo, image or alphanumeric string. The orientation features are not limited to two-dimensional features, but also include three-dimensional features.

Cable

Figure 15:
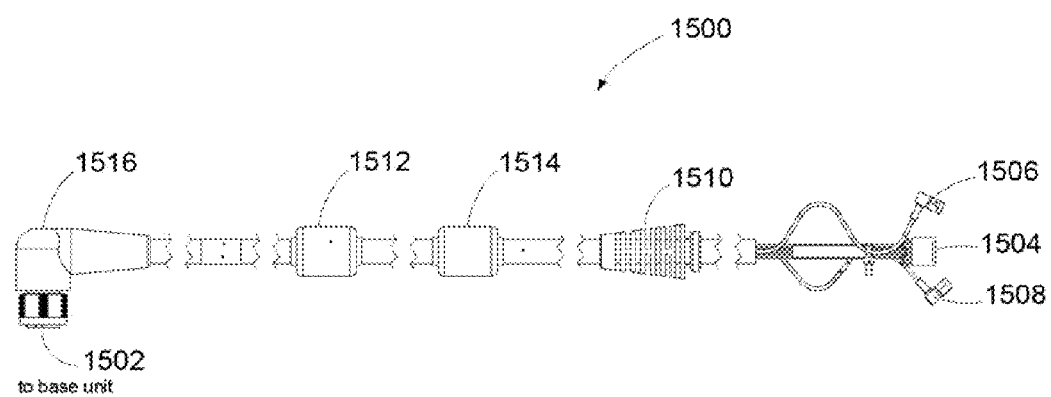
FIG. 15 illustrates an exemplary cable assembly in accordance with an embodiment of the invention.

The isolation of the energizing signal and the sensor signal provided by the base unit and the coupling loop must be maintained in the cable that connects the base unit to the coupling loop. FIG. 15 illustrates an exemplary cable 1500 that connects the base unit to the coupling loop and that isolates the energizing signal from the sensor signal. The end of the cable that connects to the base unit includes a multi-pin connector 1502 (e.g. AL06F15-ACS provided by Amphenol) and a right angle housing 1516. The end of the cable that connects to the coupling loop includes three connectors. The first connector 1504 is a multi-pin connector (e.g. AMP 1-87631-0 provided by Amphenol) that connects to the filtering and switching circuitry associated with the loop, the second connector 1506 connects to the energizing loop and the third connector 1508 connects to the loop that couples the signal from the sensor. The right angle housing 1516 and the strain relief 1510 provide strain relief at each end of the cable. When assembled with the housing, the strain relief 1510 is positioned proximate to the housing. Alternatively, other types of strain relief can be implemented, including physical constraints, such as tie wraps, ferrals or epoxy, and/or service loops. The cable also includes ferrite beads, 1512, 1514. The ferrite beads help reduce ground currents within the cable.

Figure 16:
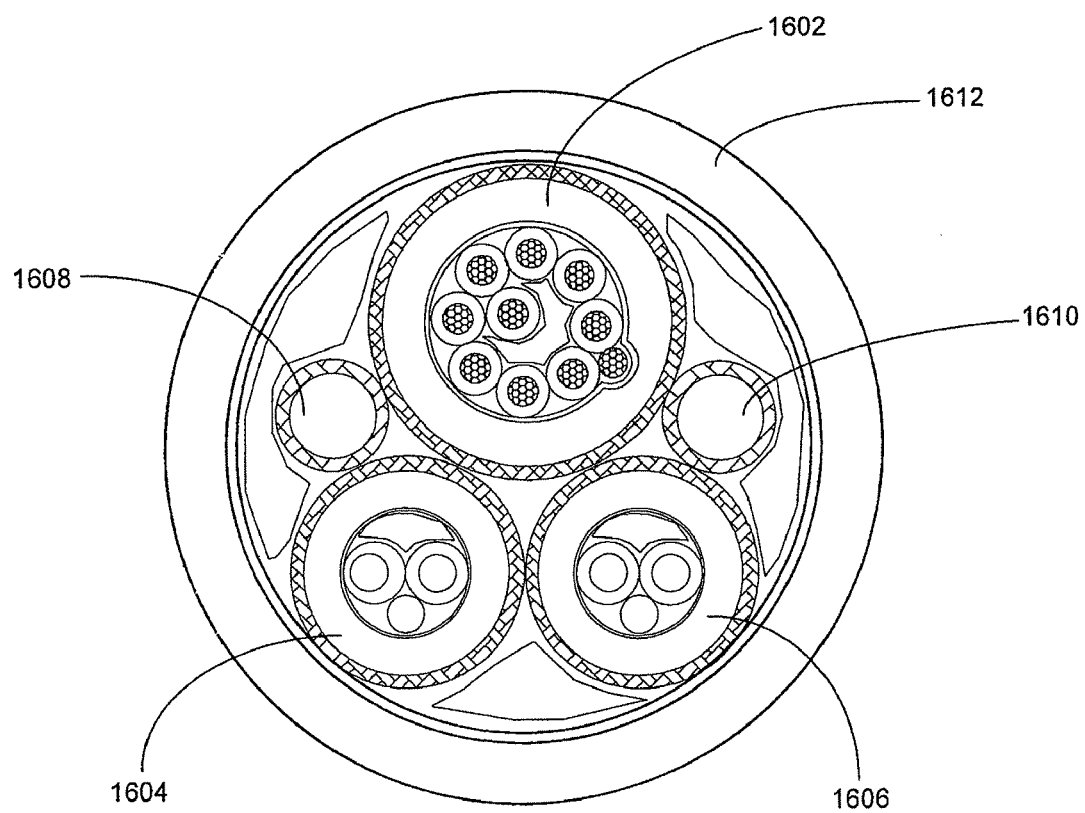
FIG. 16 illustrates an exemplary cross section of the cable assembly in accordance with an embodiment of the invention.

FIG. 16 illustrates a cross section of an exemplary cable. The cable includes an inner bundle 1602, two twisted pairs 1604, 1606, and two coaxial cables 1608, 1610. At the end of the cable that connects to the coupling loop, the inner bundle and the twisted pairs are connected to the first connector 1504 of FIG. 15, one of the coaxial cables 1610 is connected to the second connector 1506 of FIG. 15 and the other coaxial cable 1610 is connected to the third connector 1508 of FIG. 15. At the end of the cable that connects to the base unit, the inner bundle, the twisted pairs and the coaxial cables are connected to the multi-pin connector 1502 of FIG. 15. An outer sheath 1612 surrounds the inner bundle, twisted pairs, and coaxial cables.

The position of the coaxial cables within the cable is designed to maximize the isolation between the energizing signal and the sensor signal, while minimizing the diameter of the cable. The cable also is designed to maximize the isolation between the coax cable that transmits the energizing signal and the inner bundle and the twisted pairs and the coax cable that receives the sensor signal and the inner bundle. As shown in FIG. 16, the coaxial cables are located on opposite sides of the internal bundle at approximately a 180 degree angle. The isolation is maximized if a 180 degree angle is maintained between the coaxial cables. However, the invention contemplates smaller angles so long as the coaxial cables are placed on opposite sides of the internal bundle. The relative position of the coaxial cables is maintained essentially throughout the length of the cable. In some embodiments, additional braided shield surrounds the inner bundle, the twisted pairs and the coaxial cables. The additional braided shield provides additional cross talk isolation and provides a lower impedance common ground since the additional shield surrounding the coaxial cables can contact the additional shield surrounding the inner bundle.

In one embodiment, the coaxial cables are twisted around the inner bundle essentially throughout the length of the cable. Twisting the coaxial cables around the inner bundle reduces the forces exerted upon the coaxial cables and thus minimizes the potential for cable damage. The approximately 180 degree angle between the two coaxial cables is maintained essentially throughout the length of the cable. The coaxial cables can be held in position by the outer sheath, filler material, or a combination of the two.

In another embodiment, the coaxial cables are not twisted, but are attached to the internal bundle. For example, the shielding surrounding the coaxial cables is soldered to the shielding surrounding the internal bundle every six inches.

Figure 17:
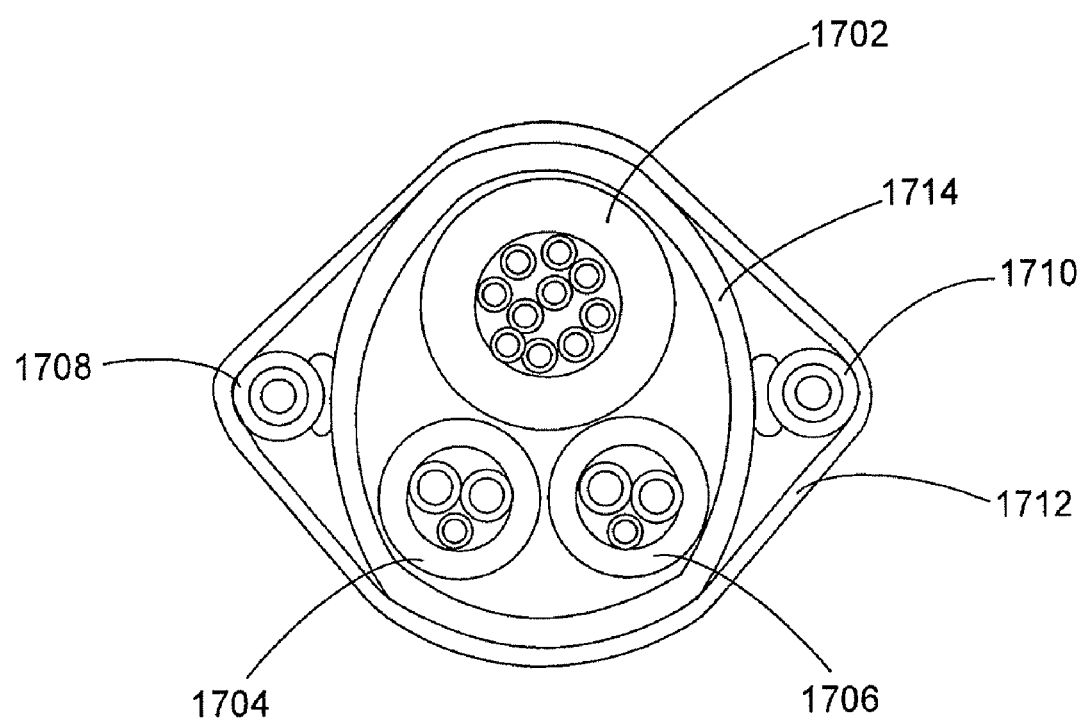
FIG. 17 illustrates another exemplary cross section of the cable assembly in accordance with an embodiment of the invention.

FIG. 17 illustrates a cross section of an alternative embodiment of the cable which includes additional shielding 1714 around the inner bundle 1702 and the twisted pairs 1704, 1706. The coaxial cables are located on opposite sides of the internal bundle at approximately a 180 degree angle and the relative position of the coaxial cables is maintained essentially throughout the length of the cable. As described above in connection with FIG. 16, additional braided shield can surround the inner bundle, twisted pairs and coaxial cables.

In the embodiment illustrated by FIG. 17, the coaxial cables 1708, 1710 are soldered to the shielding 1714 approximately every six inches throughout the length of the cable. In other embodiments that use additional shielding around the inner bundle and the twisted pairs, the outer sheath, filler material, or a combination of the two maintains the relative position of the coaxial cables.

Although the foregoing describes particular types of internal cables, the invention is applicable to any cable where two conductors are isolated with respect to one another by separating the conductors and positioning the conductors as described herein.

Additional alternative embodiments will be apparent to those skilled in the art to which the present invention pertains without departing from its spirit and scope. For example, the system can operate with different types of sensors, such as non-linear sensors that transmit information at frequencies other than the transmit frequency or sensors that use backscatter modulation. Accordingly, the scope of the present invention is described by the appended claims and is supported by the foregoing description.

What is claimed is:

1. A coupling loop assembly used for wireless communication with an implanted sensor, comprising:
    a sensor coupling loop having an inductance and connected to an input having an input impedance, wherein the input impedance is at least two times greater than an impedance of the sensor coupling loop and the sensor coupling loop is un-tuned; and
    a plurality of energizing loops arranged in parallel, for energizing the implanted sensor, each energizing loop having a different resonant frequency,
    wherein the sensor coupling loop is parallel to the energizing loops.

2. The loop assembly of claim 1, wherein the resonant frequency for a first energizing loop is approximately 31 MHz and the resonant frequency for a second energizing loop is approximately 36.3 MHz.

3. The loop assembly of claim 1, wherein there are two energizing loops and the resonant frequencies of the energizing loops are spaced geometrically.

4. The loop assembly of claim 1, wherein there are more than two energizing loops and the resonant frequencies of the energizing loops are spaced logarithmically.

5. The loop assembly of claim 1, wherein the input impedance is selected so that $$\frac{Zin}{Zin + j\omega L_1}$$

approaches 1, where Zin represents the input impedance, $L_1$ represents the inductance of the sensor coupling loop, and $\omega$ represents a frequency.

6. The loop assembly of claim 5, wherein the frequency is within a frequency range of 30 MHz to 37.5 MHz.

7. A loop assembly used for wireless communication with an implanted sensor, comprising:
    a sensor coupling loop; and
    a plurality of energizing loops, for energizing the implanted sensor, each energizing loop having a different resonant frequency, wherein the resonant frequency of one of the energizing loops is determined by a first series capacitance and the resonant frequency of a second energizing loop is determined by a second series capacitance,
    wherein the sensor coupling loop is electrically isolated from the energizing loops.

8. The loop assembly of claim 7, wherein the sensor coupling loop and the energizing loops are parallel to each other.

9. The loop assembly of claim 7, wherein there are two energizing loops and the resonant frequencies of the energizing loops are spaced geometrically.

10. The loop assembly of claim 7, wherein there are more than two energizing loops and the resonant frequencies of the energizing loops are spaced logarithmically.

11. The loop assembly of claim 7, further comprising:
    a second sensor coupling loop, wherein the sensor coupling loop and the second sensor coupling loop have different resonant frequencies.

12. A method of wireless communication using a loop assembly, comprising:
    providing an energizing signal to an implanted sensor using a plurality of tuned loops, wherein each tuned loop has a distinct resonant frequency; and
    receiving a coupled signal using an un-tuned loop connected to an input impedance that is as least two times greater than an impedance of the un-tuned loop, wherein the coupled signal is generated in response to coupling the energizing signal to a signal generating circuit,
    wherein the un-tuned loop is parallel to the tuned loops.

13. The method of claim 12, wherein the resonant frequencies of the tuned loops are selected based on a mean frequency of a desired bandwidth.

14. The method of claim 12, wherein the coupled signal is sampled less than 50 nanoseconds after the end of the energizing signal.

15. The method of claim 12, wherein each tuned loop uses a distinct series capacitance to provide the distinct resonant frequency.

* * * * *